US012667459B2

(12) United States Patent     (10) Patent No.:    US 12,667,459 B2

Nedblake                (45) Date of Patent:    *Jun. 30, 2026

(54) PENILE IMPLANT AND METHOD OF IMPLANTATION

(71) Applicant: Greydon Wesley Nedblake, St Petersburg, FL (US)

(72) Inventor: Greydon Wesley Nedblake, St Petersburg, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/289,587

(22) Filed: Aug. 4, 2025

(65) Prior Publication Data

US 2026/0124036 A1     May 7, 2026

Related U.S. Application Data

(63) Continuation of application No. 19/197,672, filed on May 2, 2025, now Pat. No. 12,453,634, which is a continuation of application No. 18/935,925, filed on Nov. 4, 2024, now Pat. No. 12,318,297.

(51) Int. Cl.
*A61F 2/26*         (2006.01)

(52) U.S. Cl.
CPC ........ *A61F 2/26* (2013.01); *A61F 2210/0009* (2013.01); *A61F 2210/0057* (2013.01); *A61F 2250/0078* (2013.01)

(58) Field of Classification Search
CPC ...... A61F 2/0036; A61F 2/004; A61F 2/0059; A61F 2/0063; A61F 2/0077; A61F 2/12; A61F 2/26; A61B 90/02
See application file for complete search history.

(56) References Cited

U.S. PATENT DOCUMENTS

| | | | | |
|---|---|---|---|---|
| 4,881,530 | A | * | 11/1989 | Trick ........................ A61F 2/26 600/40 |
| 8,545,393 | B2 | * | 10/2013 | Ellering .................... A61F 5/41 600/40 |
| 12,318,297 | B1 | | 6/2025 | Nedblake |
| 2003/0100929 | A1 | * | 5/2003 | Forsell ..................... A61F 2/26 607/39 |

(Continued)

OTHER PUBLICATIONS

International Search Report and Written Opinion in related PCT Application PCT/US2025/036594 mailed Nov. 4, 2025, 13 pages.

(Continued)

*Primary Examiner* — Carrie R Dorna
(74) *Attorney, Agent, or Firm* — Hovey Williams LLP; Kameron D. Kelly

(57) ABSTRACT

A body implantable penile prosthetic assembly includes a reservoir, a penile implant, and a pump. The reservoir is for containing a saline solution. The penile implant is penile implant operable to shift between a flaccid state in which the penile implant is at least partially depleted of the saline solution and an erect state in which the penile implant receives the saline solution from the one or more reservoirs. The pump is configured to generate pressure that causes the saline solution to flow from the reservoir to the penile implant to cause the penile implant to form the erect state. The penile implant includes a cylinder for receiving the saline solution. The cylinder is formed from a multilayered material having an inner layer comprising polyester and an outer layer comprising silicone.

18 Claims, 6 Drawing Sheets

(56)         References Cited

U.S. PATENT DOCUMENTS

2011/0288639 A1\*   11/2011   Trilokekar ................ A61F 2/12
                                                             623/8
2017/0367806 A1\*   12/2017   Gingras ................ A61L 31/005

OTHER PUBLICATIONS

Hakim, L. et al. "Emerging tools for erectile dysfunction: a role for regenerative medicine", Nature Reviews Urology, 2012, vol. 9, pp. 520-536, A abstract; pp. 520-521, 527-528, 533.

\* cited by examiner

PENILE IMPLANT AND METHOD OF IMPLANTATION

CROSS-REFERENCE TO RELATED APPLICATIONS

The current patent application is a continuation-in-part application which claims priority benefit of earlier-filed U.S. patent application Ser. No. 19/197,672; titled "PENILE IMPLANT AND METHOD OF IMPLANTATION"; and filed May 2, 2025, which is a continuation application which claims priority benefit of earlier-filed U.S. patent application Ser. No. 18/935,925; titled "PENILE IMPLANT AND METHOD OF IMPLANTATION"; and filed Nov. 4, 2024. The earlier-filed patent applications are hereby incorporated by reference, in their entireties, into the current patent application.

BACKGROUND OF THE INVENTION

A penile implant is often a solution when a patient has not effectively responded to erectile dysfunction medications or vacuum constriction devices. Generally, a penile implant includes a cylinder that is either bendable or inflatable for simulating an erection. However, in some circumstances, the exterior surface of the cylinder adheres to or rubs against internal portions of the shaft of the penis. This causes discomfort and, in some cases, infection. Thus, there is a need for improved penile implants.

This background discussion is intended to provide information related to the present invention which is not necessarily prior art.

SUMMARY OF THE INVENTION

Embodiments of the current invention address one or more of the above-mentioned problems and provide a distinct advance in the art of penile implants and procedures for performing penile implant surgery.

A body implantable penile prosthetic assembly according to an embodiment of the invention includes a reservoir, a penile implant, and a pump. The reservoir is for containing a saline solution. The penile implant is operable to shift between a flaccid state in which the penile implant is partially depleted of the saline solution and an erect state in which the penile implant receives the saline solution from the one or more reservoirs. The pump is configured to generate pressure that causes the saline solution to flow from the reservoir to the penile implant to cause the penile implant to form the erect state. The penile implant includes a cylinder for receiving the saline solution. The cylinder is formed from a multilayered material having an inner layer comprising polyester and an outer layer comprising silicone.

Another embodiment of the invention is a method of providing a patient with a body implantable penile prosthetic. The method includes inserting a reservoir into the abdomen of the patient; inserting a penile implant into a corpus cavernosum of the patient; and inserting a pump operable to be in fluid communication with the reservoir and the penile implant. The pump is configured to generate pressure that causes saline solution to flow from the reservoir to the penile implant to cause the penile implant to form an erect state. The penile implant includes a cylinder for receiving the saline solution. The cylinder is formed from a multilayered material having an inner layer comprising polyester and an outer layer comprising silicone.

Another embodiment of the invention is a body implantable penile prosthetic implant. The body implantable penile prosthetic implant includes a cylinder and a stem cell coating. The cylinder is for receiving saline solution and is formed of a multilayer material comprising an inner layer having polyester and an outer layer having silicone. The stem cell coating is attached to the outer layer having silicone.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing FIGURES.

BRIEF DESCRIPTION OF DRAWINGS

Embodiments of the current invention are described in detail below with reference to the attached drawing FIGURES, wherein.

Figure 1:
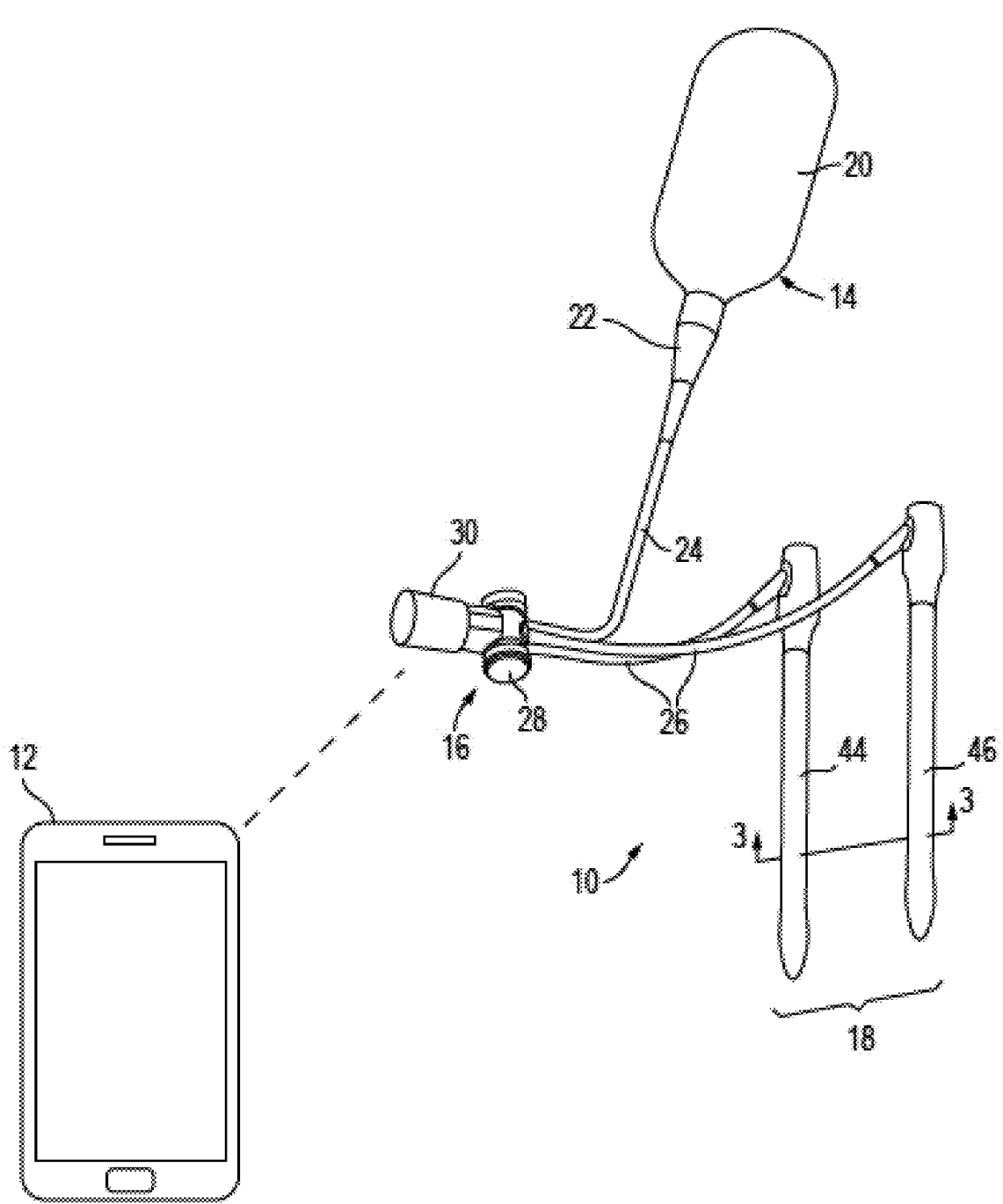
FIG. 1 is a body implantable penile prosthetic assembly constructed in accordance with an embodiment of the present invention.

The drawing FIGURES do not limit the current invention to the specific embodiments disclosed and described herein. The drawings are not necessarily to scale, emphasis instead being placed upon clearly illustrating the principles of the invention.

DETAILED DESCRIPTION OF THE INVENTION

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

Turning to FIG. 1, a body implantable penile prosthetic assembly 10 constructed according to an embodiment of the invention is depicted. The penile prosthetic assembly 10 may be configured for communication with a remote device 12. The remote device 12 may be a smart phone, remote controller, tablet, laptop, or the like. The penile prosthetic assembly 10 is operable to be implanted in the body of a patient and includes one or more reservoirs 14, one or more pumps 16, and a penile implant 18.

Figure 5:
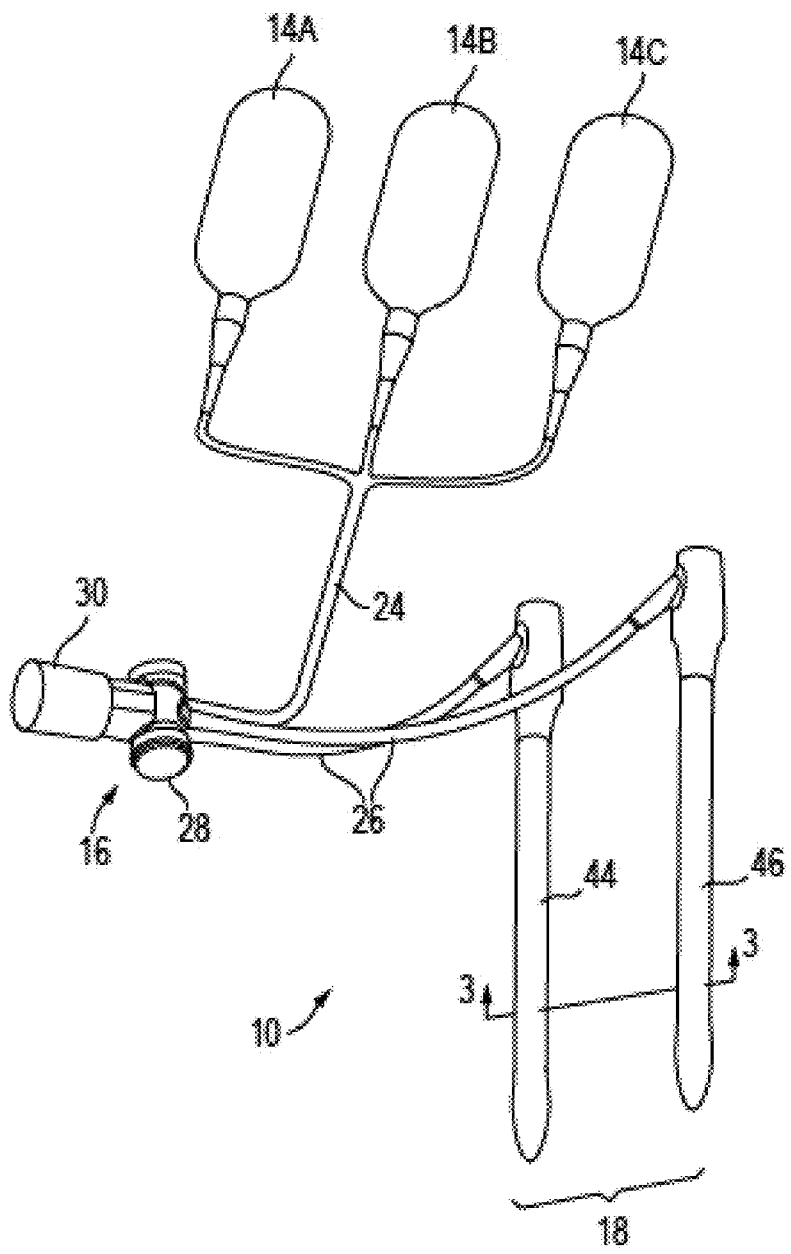
FIG. 5 is the body implantable penile prosthetic assembly of FIG. 1 having three reservoirs.
Figure 6:
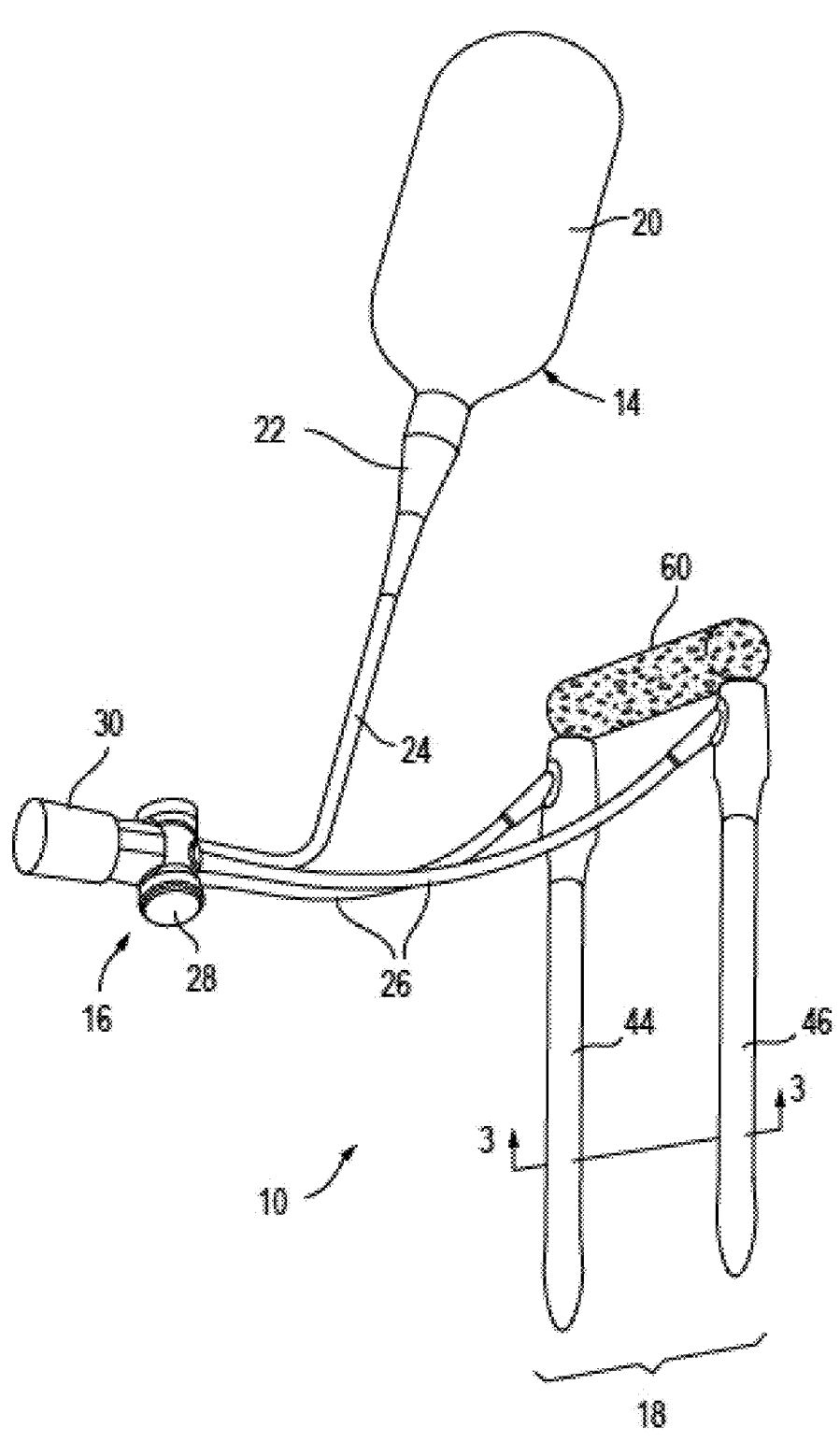
FIG. 6 is the body implantable penile prosthetic assembly of FIG. 1 having an absorbent portion disposed at proximal ends of cylinders of the assembly.

The reservoir 14 is for containing a fluid medium, such as water, a liquid saline solution or the like, and/or any other suitable alternative, that can be transferred back and forth between the penile implant 18 and the reservoir 14. The reservoir 14 includes a main body 20 and an outlet 22. One or more conduits 24 (such as kink-resistant, flexible tubing) is connected to the outlet 22 and the pump 16 so that the fluid-containing body 20 of the reservoir 14 is in fluid communication with the pump 16. In one or more embodiments, the reservoir 14 is sized to be placed in the abdomen of the patient, such as in a submuscular region. However, it is foreseen that the reservoir 14 is sized to be placed in other regions of the body without departing from the scope of the present invention. Further, in one or more embodiments, the assembly 10 includes at least three reservoirs 14A, 14B, 14C (as depicted in FIG. 5) to reduce the size of the incision required to implant the reservoirs in the patient.

The pump 16 is configured to supply pressure that helps direct the fluid from the reservoir 14 into the penile implant 18 so that the penile implant 18 forms an erect state. The pump 16 is configured to direct the fluid from the reservoir 14 into the penile implant 18 so that the penile implant 18 forms the erect state. In one or more embodiments, the pump 16 is also configured to reverse flow so that the fluid is directed from the penile implant 18 back into the reservoir 14 form a flaccid state. In one or more embodiments, the pump 16 is configured to direct the fluid from the penile implant 18 into the reservoir 14 so that the penile implant 18 forms a flaccid state. The pump 16 may be any type of pump without departing from the scope of the present invention. For example, the pump 16 may be a centrifugal pump, diaphragm pump, gear pump, piston pump, lobe pump, direct drive pump, peristaltic pump, piezoelectric pump, or the like.

One or more conduits 26 (such as kink-resistant, flexible tubing) are connected to the pump 16 and the penile implant 18 so that the pump 16 is in fluid communication with the penile implant 18.

In one or more embodiments, the pump 16 includes a button 28 configured to cause the pump 16 to direct fluid from the reservoir 14 to the penile implant 18 or vice versa and a pump housing 30 connected to and housing a portion of the button 28. The button 28 may be any type of user input without departing from the scope of the present invention. For example, the button 28 may be a push button, a toggle switch, a rocker switch, a dome switch, a membrane switch, a tactile switch, a pressure switch, a push valve, a release valve, or the like.

Figure 2:
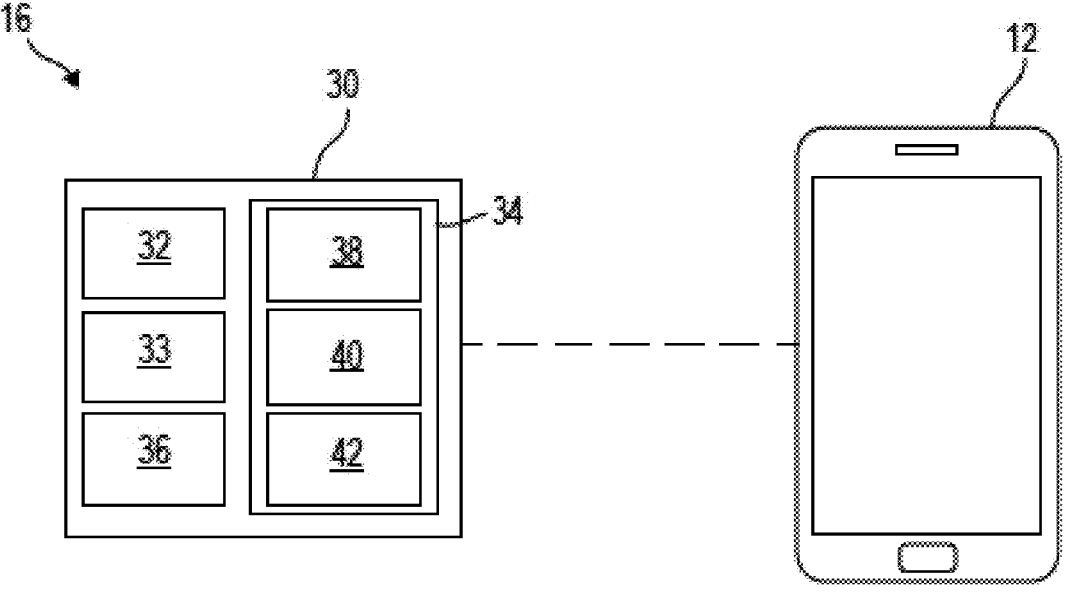
FIG. 2 illustrates various components of a pump of the penile prosthetic assembly of FIG. 1 shown in block schematic form.

Turning to FIG. 2, in one or more embodiments, the pump 16 includes one or more motors 32, one or more valves 33, a controller 34, and a power source 36. The motor(s) 32 may be an electrical motor operable to provide the pressure for directing the fluid between the reservoir 14 and the implant 18. The one or more valves 33 may be configured to allow the pressurized fluid back into the reservoir 14 and/or to allow pressurized fluid from the reservoir 14 into the implant 18. The valve(s) 33 may be any type of valve known in the art, such as a release valve, a ball valve, a check valve, a needle valve, a diaphragm valve, a gate valve, a pinch valve, a solenoid valve, a motorized ball valve, a piezoelectric valve, a proportional valve, a stepper motor actuated valve, or the like.

Example pumps, motors, and valves are described and depicted in U.S. Pat. No. 8,545,393, U.S. Patent Application Publication No. 2023/0293302, and U.S. Pat. No. 10,383, 715, which are hereby incorporated by reference herein.

In one or more embodiments, the controller 34 comprises a communication element 38, a memory element 40, and a processing element 42. The communication element 38 may generally allow communication with systems or devices external to the pump 16. The communication element 38 may include signal or data transmitting and receiving circuits, such as antennas, amplifiers, filters, mixers, oscillators, digital signal processors (DSPs), and the like. The communication element 38 may establish communication wirelessly by utilizing RF signals and/or data that comply with communication standards such as cellular 2G, 3G, 4G, 5G, or LTE, WiFi, WiMAX, Bluetooth®, BLE, or combinations thereof. The communication element 38 may be in communication with the processing element 42 and the memory element 40.

The memory element 40 may include data storage components, such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 40 may be embedded in, or packaged in the same package as, the processing element 42. The memory element 40 may include, or may constitute, a "computer-readable medium". The memory element 40 may store the instructions, code, code segments, software, firmware, programs, applications, apps, services, daemons, or the like that are executed by the processing element 42.

The processing element 42 may include processors, microprocessors (single-core and multi-core), microcontrollers, DSPs, field-programmable gate arrays (FPGAs), analog and/or digital application-specific integrated circuits (ASICs), or the like, or combinations thereof. The processing element 42 may generally execute, process, or run instructions, code, code segments, software, firmware, programs, applications, apps, processes, services, daemons, or the like. The processing element 42 may also include hardware components such as finite-state machines, sequential and combinational logic, and other electronic circuits that can perform the functions necessary for the operation of the current invention. The processing element 42 may be in communication with the other electronic components through serial or parallel links that include address busses, data busses, control lines, and the like.

The communication element 38 is configured to receive a wireless signal representative of an instruction to switch states of the implant 18. For example, the current state of the implant 18 may be stored on the memory element 40, and the communication element 38 may receive the signal representative of an instruction to switch states of the implant from, e.g., the remote device 12, and/or the button 28 may be engaged. The communication element 38 may relay the signal to the processing element 42, and/or the processing element 38 may receive a signal as a result of the button 28 being engaged. The processing element 42 may be configured to check the current state of the implant 18 as stored in the memory element 40 and send a signal to the motor(s) 32 and/or solenoid valve(s) 33 based upon the current state of the implant 18. For example, in one or more embodiments, if the current state is a flaccid state, then the processing element 42 may be configured to send an instruction to the motor(s) 32 to supply the pressure for directing the fluid from the reservoir 14 to the implant 18 to form the erect state. Additionally or alternatively, the processing element 42 may be configured to send an instruction to the solenoid valve(s) 33 to open and allow pressurized fluid to flow from the reservoir 14 to the implant 18. If the current state is the erect state, then the processing element 42 may be configured to send an instruction to the motor(s) 32 to direct the fluid so that it flows from the implant 18 to the reservoir 14 to form the flaccid state. Additionally or alternatively, the processing element 42 may be configured to send an instruction to the solenoid valve(s) 33 to open and allow pressurized fluid to flow from the implant 18 to the reservoir 14. The motor(s) 32, valve(s) 33, and controller 34 may be configured any number of ways using any kind of logic without departing from the scope of the present invention. In one or more embodiments, the pump 16 may be configured to provide a wider range of pressure due to the material of the penile implant 18, as discussed in further detail below. In one or more embodiments, the pump 16 is configured provide a pressure of at least 50 kilopascal (kPa) up to about 27 kPa.

In one or more embodiments, the signal may include a unique code and/or have a predefined frequency. The unique code and/or frequency may be stored on the memory element 40. The processing element 42 may employ other algorithms or processes for detecting the current state of the implant 18, directing the motor(s) 32 and/or valve(s) 33, and/or otherwise causing the implant 18 to switch states without departing from the scope of the present invention. The assembly 10 may use any other suitable means for changing states of the implant 18 without departing from the scope of the present invention.

The power source 36 provides electrical energy to the motor(s) 32, the valve(s) 33, and the controller 34. In one or more embodiments, the power source 36 comprises one or more energy storage devices, such as a battery, a capacitor, an ultracapacitor, a structural capacitor, or the like. The energy storage devices may be replaceable devices that are readily disconnected and replaced via a minor surgical procedure. Additionally or alternatively, the power source 36 includes a wireless charging system configured capture a electromagnetic signal and convert it to electric current for storage on the energy storage devices and/or supplying to the motor and/or the controller 34. An example power source with a wireless charging system is described and depicted in U.S. Patent Application Publication No. 2023/0293302, which is incorporated by reference herein.

In one or more embodiments, the pump 16 is sized to be placed in the scrotum of the patient. However, it is foreseen that the pump 16 is sized to be placed in other regions of the body without departing from the scope of the present invention. For example, in one or more embodiments, the pump 16 may not include the button 28 and is integrated with the reservoir 14 to preserve space and minimize the invasiveness of the surgery. While the pump 16 is described and depicted as being an electrical pump, the pump 16 may be any other type of pump known in the art, including a manual pump as described and depicted in U.S. Pat. No. 8,545,393, which is incorporated by reference herein.

Figure 3:
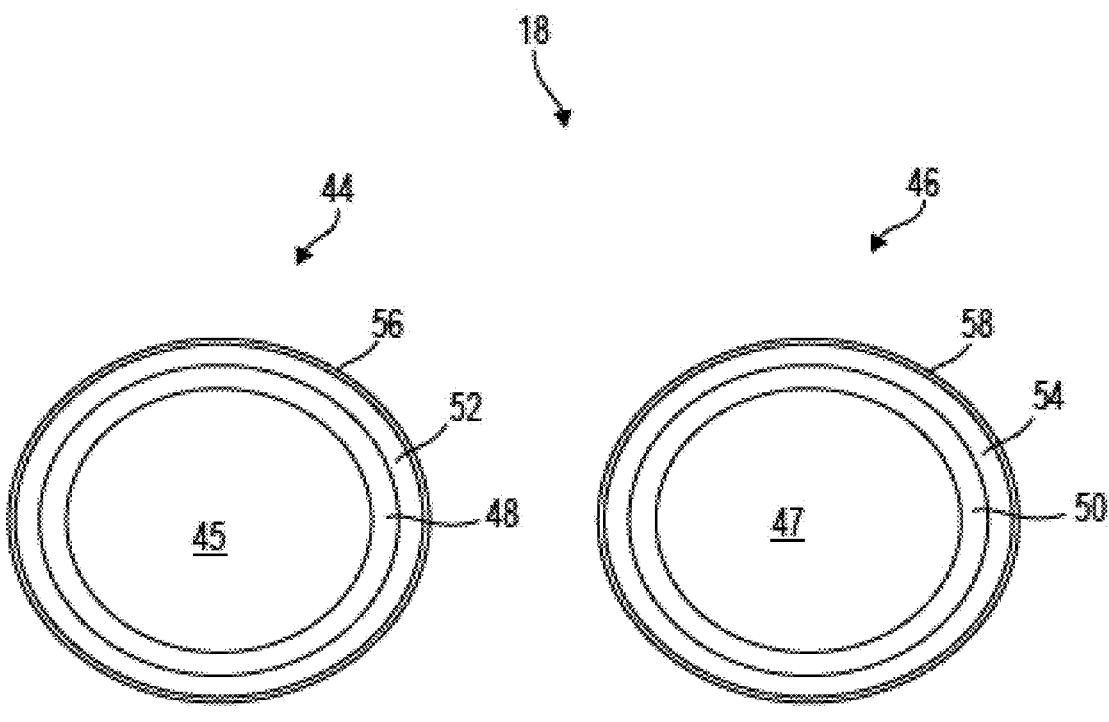
FIG. 3 is a section view of cylinders of the penile prosthetic assembly of FIG. 1 viewed along lines 3-3 of FIG. 1.

Turning back to FIG. 1, the penile implant 18 is operable to receive the saline solution to form the erect state. In one or more embodiments, the penile implant 18 includes a pair of cylinders 44, 46. The cylinders 44, 46 may be inflatable bladders with flexible or extensible walls, semi-rigid walls, and/or rigid walls that define an internal chamber. Turning to FIG. 3, in one or more embodiments, each cylinder 44, 46 of the penile implant 18 includes chambers 45, 47 defined by one or more layers 48, 50 at least partially made of polyester. The chambers 45, 47 are operable to receive the fluid from the reservoir 14. In one or more embodiments, the one or more layers 48, 50 comprise biaxially oriented polyester. In one or more embodiments, the layers 48, 50 are made of one or more polyester sheets having a thickness of around 5.08 microns (20 Gauge) up to around 17.78 microns (70 Gauge). In one or more embodiments, the layers 48, 50 are made of one or more polyester sheets having a thickness of less than 17.78 microns (70 Gauge). In one or more embodiments, the layers 48, 50 are made of one or more polyester sheets having a thickness of around 10.16 microns (40 Gauge) up to around 15.24 microns (60 Gauge). The cylinders 44, 46 made of polyester enable a wider range of pressure to be used to inflate the cylinders 44, 46. In one or more embodiments, the layers 48, 50 form seamless cylinders made from of one or more polyester sheets that are cut and/or sealed using one or more lasers, such as one or more continuous wave lasers or any other suitable laser and/or means for cutting and scaling to form a seamless product.

The cylinders 44, 46 may be sized according to patient needs and physical parameters. The cylinders 44, 46 may be sized to contain about 50 cubic centimeters (cc) of fluid up to around 150 cc. However, due to the extensibility of the cylinders 44, 46 comprising polyester, the volume can be more or less depending on the needs of a patient.

In one or more embodiments, each cylinder 44, 46 further comprises one or more layers 52, 54 comprising silicone and exterior coatings 56, 58 of stem cells. The layers 52, 54 comprising silicone are disposed on the exterior surface of the polyester layers 48, 50. The polyester cylinders 48, 50 may be coated with silicone and cured to form the silicone layers 52, 54. In one or more embodiments, the silicone layers 52, 54 comprise polydimethylsiloxane (PDMS). In one or more embodiments, one or more of the silicone layers 52, 54 comprises an inert, organic bio-silicone.

In one or more embodiments, the layers 52, 54 comprising silicone are configured to receive the stem cell coatings 56, 58. As used herein, "configured to receive a stem cell coating" means the silicone is altered in such a way to make it conducive for receiving the stem cell coating, such as through application of an acid and/or adhesive, by plasma treating the silicone layers 52, 54, and/or by treating the silicone layers 52, 54 with lasers (such as yttrium-aluminum-garnet (YAG) lasers). In one or more embodiments, peptides are applied to the silicone layers 52, 54 for increased adhesion between the silicone 52, 54 and stem cells 56, 58. In one or more embodiments, this involves activating the exterior surface of the silicone layers 52, 54 and applying cross-linking molecules so that the peptide layers may be covalently grafted to the silicone layers 52, 54. Additionally or alternatively, the silicone layers 52, 54 may be treated with an acid, such as itaconic acid, for stabilizing the stem cell coatings 56, 58, as discussed below. The silicone layers 52, 54 may be treated any number of ways without departing from the scope of the present invention, including as described in "Silicone Grafted Bioactive Peptides and their Applications" by Martin et al. and published in Current Opinion in Chemical Biology, Volume 52 (2019), which is hereby incorporated by reference herein. The peptides may be any type of suitable peptide without departing from the scope of the invention, including monopeptides, polylysine or other homopolypeptides, polypeptides, oligopeptides, peptide fragments, lipopeptide, or the like. In one or more embodiments, the peptides are silylated.

The stem cells of the stem cell coatings 56, 58 may comprise any type of stem cell known in the art without departing from the scope of the present invention, including somatic stem cells, induced pluripotent stem cells, or the like. In one or more embodiments, the stem cell coatings 56, 58 comprise mesenchymal stem cells, such as human adipose-derived stem cells. Methods of stabilizing stem cells on silicone structures are described in "Assessment of Human Adipose-Derived Stem Cell on Surface-Modified Silicone Implant to Reduce Capsular Contracture Formation" by Sutthiwanjampa et al. and published in Bioengineering and Translational Medicine (2021), which is hereby incorporated by reference herein.

In one or more embodiments, the penile implant 18 is sized to be placed in the shaft of the penis, and in particular, the cylinders 44, 46 are sized to be inserted into the corpora cavernosa of the shaft.

In one or more embodiments, the body implantable penile prosthetic assembly 10 further includes one or more resilient material 60 disposed at the distal ends of the cylinders 44, 46. The portion 60 may comprise an absorbent and/or porous material, such as a sponge, piece of fabric, or the like. The portion 60 may be attached to the distal ends of the cylinders 44, 46 and/or positioned in place during implantation in the patient's body during the surgery. The portion 60 is configured to provide cushioning and/or shock absorption against the cylinders 44, 46 to dampen or absorb movement of the cylinders 44, 46 to inhibit discomfort.

In use, once the body implantable penile prosthetic assembly 10 has been implanted in the patient, the patient can selectively switch states of the implant 18. If the implant 18 is in a flaccid state, the patient may press the button 28 and/or send a signal via the remote device 12 in wireless communication with the pump 16. The pump 16 activates to direct fluid from the reservoir 14 to the implant 18 until the implant 18 forms the erect state. For example, the communication element 38 may receive the signal from the remote device 12 and/or the button 28. The communication element 38 may relay the instruction to the processing element 42, which checks the current state as stored on the memory element 40, and then directs the motor(s) 32 and/or the valve(s) 33 of the pump 16 accordingly. The processing element 42 may be configured to activate the motor(s) 32 and/or the valve(s) 33 for a predetermined amount of time and/or it may receive a signal from one or more sensors indicative of a metric associated with a volume of the fluid in the implant 18 and/or a volume of the fluid remaining in the reservoir 14.

To switch back to the flaccid state, the patient may press the button 28 and/or send a signal via the remote device 12 in wireless communication with the pump 16. The pump 16 may then reverse its previous operation and pull the fluid from the implant 18 and direct it to the reservoir 14. The power source 36 may provide electric power to the pump 16 and be recharged via a wireless charging system.

Figure 4:
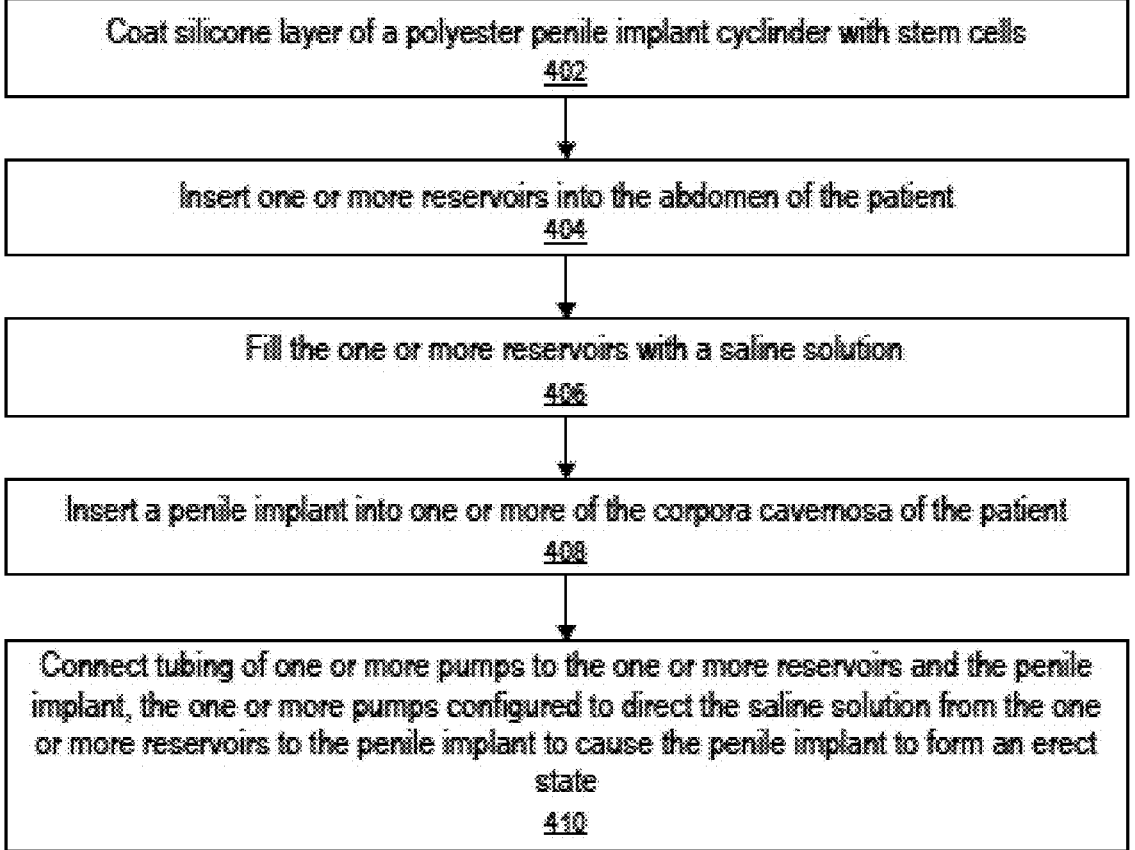
FIG. 4 illustrates at least a portion of the steps of an exemplary method of providing a patient with a body implantable penile prosthetic in accordance with embodiments of the present invention.

The flow chart of FIG. 4 depicts the steps of an exemplary method 400 of providing a patient with a body implantable penile prosthetic. In some alternative implementations, the functions noted in the various blocks may occur out of the order depicted in FIG. 4. For example, two blocks shown in succession in FIG. 4 may in fact be executed substantially concurrently, or the blocks may sometimes be executed in the reverse order depending upon the functionality involved. In addition, some steps may be optional. The method 400 is described below, for ease of reference, as being performed in relation to the body implantable penile prosthetic assembly 10 illustrated in FIGS. 1-3. However, the method 400 may be performed with a different penile prosthetic assembly without departing from the scope of the present invention.

Referring to step 402, the stem cell coating is applied to the exterior surface of the layer of the cylinder comprising silicone. This step may include extracting stem cells from the patient, such as from one or more lipoaspirates. In one or more embodiments, this step includes plasma treating the exterior surface of the layer comprising silicone prior to applying the stem cell coating. Alternatively or additionally, this step includes applying an acid and/or adhesive to the silicone layer. Alternatively or additionally, this step includes applying one or more peptides to the plasma treated exterior surface of the layer comprising silicone prior to applying the stem cell coating.

Referring to step 404, the reservoir is inserted into the abdomen of the patient. This step may include forming one or more incisions in the patient, forming a cavity in the abdomen (such as in a submuscular region), and performing sanitation procedures to avoid infection.

Referring to step 406, the reservoir is filled with a fluid, such as a saline solution. This step may include attaching the tubing to the reservoir and using a clamp on the tubing to prevent the fluid from exiting the reservoir.

Referring to step 408, the cylinders of the penile implant are inserted into the corpora cavernosa of the patient. This step may include forming cavities in the corpora cavernosa of the patient. This step may further include using one or more cylindrical guides to position the cylinders of the penile implant into the cavities formed in the corpora cavernosa.

Referring to step 410, tubing is connected to the pump, the reservoir, and the penile implant. As discussed above, the pump is configured to direct the saline solution from the reservoir to the penile implant to cause the penile implant to form the erect state and to direct the saline solution out of the penile implant to form the flaccid state. This step may include electrically connecting the power system to the electrical motor and the controller. In one or more embodiments, this step includes connecting, or pairing, the communication element with the remote device. This step may include forming an incision in the scrotum and/or at the base of the scrotum of the patient and inserting the pump into the scrotum.

Throughout this specification, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current invention can include a variety of combinations and/or integrations of the embodiments described herein.

Although the present application sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments may be implemented, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

In various embodiments, computer hardware, such as a processing element, may be implemented as special purpose or as general purpose. For example, the processing element may comprise dedicated circuitry or logic that is permanently configured, such as an application-specific integrated circuit (ASIC), or indefinitely configured, such as an FPGA, to perform certain operations. The processing element may also comprise programmable logic or circuitry (e.g., as encompassed within a general-purpose processor or other programmable processor) that is temporarily configured by software to perform certain operations. It will be appreciated that the decision to implement the processing element as special purpose, in dedicated and permanently configured circuitry, or as general purpose (e.g., configured by software) may be driven by cost and time considerations.

Accordingly, the term "processing element" or equivalents should be understood to encompass a tangible entity, be that an entity that is physically constructed, permanently configured (e.g., hardwired), or temporarily configured (e.g., programmed) to operate in a certain manner or to perform certain operations described herein. Considering embodiments in which the processing element is temporarily configured (e.g., programmed), each of the processing elements need not be configured or instantiated at any one instance in time. For example, where the processing element comprises a general-purpose processor configured using software, the general-purpose processor may be configured as respective different processing elements at different times. Software may accordingly configure the processing element to constitute a particular hardware configuration at one instance of time and to constitute a different hardware configuration at a different instance of time.

Computer hardware components, such as communication elements, memory elements, processing elements, and the like, may provide information to, and receive information from, other computer hardware components. Accordingly, the described computer hardware components may be regarded as being communicatively coupled. Where multiple of such computer hardware components exist contemporaneously, communications may be achieved through signal transmission (e.g., over appropriate circuits and buses) that connect the computer hardware components. In embodiments in which multiple computer hardware components are configured or instantiated at different times, communications between such computer hardware components may be achieved, for example, through the storage and retrieval of information in memory structures to which the multiple computer hardware components have access. For example, one computer hardware component may perform an operation and store the output of that operation in a memory device to which it is communicatively coupled. A further computer hardware component may then, at a later time, access the memory device to retrieve and process the stored output. Computer hardware components may also initiate communications with input or output devices, and may operate on a resource (e.g., a collection of information).

The various operations of example methods described herein may be performed, at least partially, by one or more processing elements that are temporarily configured (e.g., by software) or permanently configured to perform the relevant operations. Whether temporarily or permanently configured, such processing elements may constitute processing element-implemented modules that operate to perform one or more operations or functions. The modules referred to herein may, in some example embodiments, comprise processing element-implemented modules.

Similarly, the methods or routines described herein may be at least partially processing element-implemented. For example, at least some of the operations of a method may be performed by one or more processing elements or processing element-implemented hardware modules. The performance of certain of the operations may be distributed among the one or more processing elements, not only residing within a single machine, but deployed across a number of machines. In some example embodiments, the processing elements may be located in a single location (e.g., within a home environment, an office environment or as a server farm), while in other embodiments the processing elements may be distributed across a number of locations.

Unless specifically stated otherwise, discussions herein using words such as "processing," "computing," "calculating," "determining," "presenting," "displaying," or the like may refer to actions or processes of a machine (e.g., a computer with a processing element and other computer hardware components) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus.

The patent claims at the end of this patent application are not intended to be construed under 35 U.S.C. § 112(f) unless traditional means-plus-function language is expressly recited, such as "means for" or "step for" language being explicitly recited in the claim(s).

Although the technology has been described with reference to the embodiments illustrated in the attached drawing FIGURES, it is noted that equivalents may be employed and substitutions made herein without departing from the scope of the technology as recited in the claims.

Having thus described various embodiments of the technology, what is claimed as new and desired to be protected by Letters Patent includes the following:

The invention claimed is:

1. A body implantable penile prosthetic assembly comprising:

one or more reservoir for containing a fluid;

a penile implant operable to shift between an erect state in which the penile implant receives a volume of the fluid from the one or more reservoir and a flaccid state in which at least a portion of the volume of the fluid exits the penile implant; and one or more pump configured to generate pressure for causing the volume of the fluid to flow from the one or more reservoir to the penile implant to shift the penile implant to the erect state, wherein the penile implant comprises one or more bladder for receiving the volume of the fluid, the one or more bladder being formed from a multilayered material having an inner layer comprising a polymeric material, an outer layer comprising silicone, and a stem cell coating operatively associated with the outer layer.

2. The body implantable penile prosthetic assembly of claim 1, wherein the outer layer is configured to receive the stem cell coating via at least one of an application of an acid, an application of adhesive, a plasma treatment, or a laser treatment.

3. The body implantable penile prosthetic assembly of claim 1, wherein the stem cell coating comprises human adipose-derived stem cells.

4. The body implantable penile prosthetic assembly of claim 1, further comprising one or more portion comprising a resilient portion operatively associated with a proximal end of the one or more bladder.

5. The body implantable penile prosthetic assembly of claim 1, wherein the one or more pump comprises one or more electrical motor, further comprising a controller in communication with the one or more electrical motor, the controller comprising a wireless communication element configured to receive a wireless signal representative of an instruction to cause the penile implant to form the erect state.

6. The body implantable penile prosthetic assembly of claim 5, further comprising one or more energy storage device electrically connected to the controller and the one or more electrical motor.

7. The body implantable penile prosthetic assembly of claim 5, further comprising a wireless charging system configured to receive an electromagnetic signal and convert the electromagnetic signal to electric current for supplying to the one or more electrical motor.

8. The body implantable penile prosthetic assembly of claim 1, wherein the penile implant includes one or more additional bladders.

9. The body implantable penile prosthetic assembly of claim 1, wherein the polymeric material comprises biaxially oriented polyester.

10. A method of providing a patient with the body implantable penile prosthetic of claim 1, the method comprising:

inserting the one or more reservoir into the abdomen of the patient;

inserting the penile implant into one or more of the corpora cavernosa of the patient;

inserting the one or more pump into at least one of the abdomen or the scrotum of the patient.

11. The method of claim 10, further comprising applying the stem cell coating to the exterior surface of the layer comprising silicone before inserting the penile implant.

12. The method of claim 11, further comprising plasma treating the exterior surface of the layer comprising silicone prior to applying the stem cell coating.

13. The method of claim 12, further comprising applying one or more peptides to the plasma treated exterior surface of the layer comprising silicone prior to applying the stem cell coating.

14. The method of claim 10, wherein the one or more pump comprises one or more electrical motor, further comprising electrically connecting a controller in communication with the one or more electrical motor, the controller comprising a wireless communication element configured to receive a wireless signal representative of an instruction to cause the penile implant to shift to the erect state.

15. The method of claim 14, further comprising electrically connecting one or more energy storage device to the controller and the one or more electrical motor.

16. A body implantable penile prosthetic assembly comprising:

one or more reservoir for containing a fluid;

a penile implant operable to shift between an erect state in which the penile implant receives a volume of the fluid from the one or more reservoir and a flaccid state in which at least a portion of the volume of the fluid exits the penile implant; and one or more pump configured to generate pressure for causing the volume of the fluid to flow from the one or more reservoir to the penile implant to shift the penile implant to the erect state, wherein the penile implant comprises two or more bladders for receiving the volume of the fluid, each of the two or more bladders being formed from a multilayered material having an inner layer comprising polymeric material having a thickness less than 17.78 microns, an outer layer comprising silicone, and a stem cell coating operatively associated with the outer layer.

17. The body implantable penile prosthetic assembly of claim 16, wherein the one or more pump comprises one or more electrical motor, further comprising a controller in communication with the one or more electrical motor, the controller comprising a wireless communication element configured to receive a wireless signal representative of an instruction to cause the penile implant to form the erect state.

18. The body implantable penile prosthetic assembly of claim 17, wherein the one or more reservoir includes at least three reservoirs.

* * * * *